United States Patent [19]

Loveland

[11] Patent Number: 4,743,249
[45] Date of Patent: May 10, 1988

[54] DERMAL AND TRANSDERMAL PATCHES HAVING A DISCONTINUOUS PATTERN ADHESIVE LAYER

[75] Inventor: Frederic D. Loveland, Suffern, N.Y.
[73] Assignee: Ciba-Geigy Corp., Ardsley, N.Y.
[21] Appl. No.: 61,024
[22] Filed: Jun. 10, 1987

Related U.S. Application Data

[63] Continuation of Ser. No. 829,636, Feb. 14, 1986, abandoned.

[51] Int. Cl.⁴ .............................................. A61F 7/02
[52] U.S. Cl. .................................. 424/447; 604/307; 604/304; 128/156
[58] Field of Search ............................. 604/896–897, 604/304, 307; 128/156

[56] References Cited

U.S. PATENT DOCUMENTS

| | | | |
|---|---|---|---|
| 2,399,545 | 4/1946 | Davis | 128/156 |
| 3,598,122 | 8/1971 | Zaffaroni . | |
| 3,598,123 | 8/1971 | Zaffaroni . | |
| 3,731,683 | 5/1973 | Zaffaroni . | |
| 3,734,097 | 5/1973 | Zaffaroni . | |
| 3,742,951 | 7/1973 | Zaffaroni . | |
| 3,797,494 | 3/1974 | Zaffaroni . | |
| 3,811,438 | 5/1974 | Economon | 128/156 |
| 3,870,041 | 3/1975 | Davies | 128/156 |
| 3,996,934 | 12/1976 | Zaffaroni . | |
| 4,219,019 | 8/1980 | Coates | 128/156 |
| 4,297,995 | 11/1981 | Golub | 604/897 |
| 4,341,208 | 7/1982 | Gordon | 604/897 |
| 4,402,696 | 9/1983 | Gulko | 604/897 |
| 4,699,792 | 10/1987 | Nick et al. | 424/446 |

OTHER PUBLICATIONS

Strategic Technologies (1985), pp. 92–98.

Primary Examiner—C. Fred Rosenbaum
Assistant Examiner—Gene B. Kartchner
Attorney, Agent, or Firm—Michael W. Glynn; Irving M. Fishman

[57] ABSTRACT

Dermal and transdermal patches having a discontinuous pattern printed adhesive layer on a first surface of an active-agent porous membrane, a non-porous backing layer in contact with a second surface of said porous membrane, opposite said first surface so as to define a compartment capable of containing an active agent or formulation thereof therein, an active-agent or formulation thereof within said compartment, and a protective overlayer on said adhesive layer distal to said porous membrane.

28 Claims, 1 Drawing Sheet

U.S. Patent  May 10, 1988  4,743,249
FIG.1
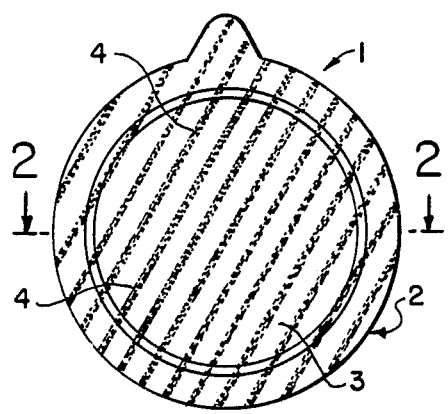
FIG.3
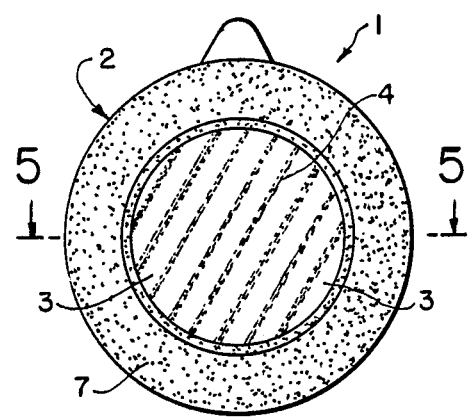
FIG.2
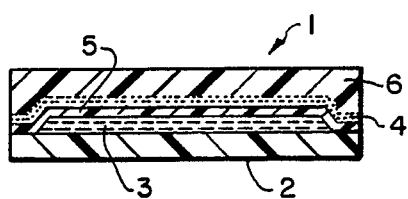
FIG.4
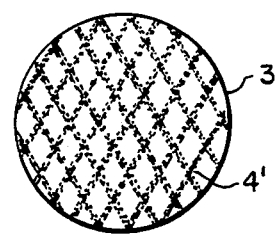
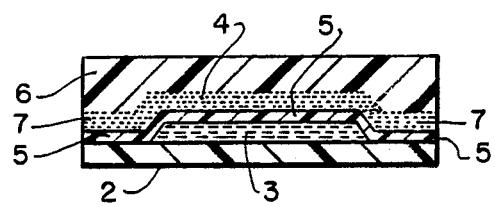
FIG.5

DERMAL AND TRANSDERMAL PATCHES HAVING A DISCONTINUOUS PATTERN ADHESIVE LAYER

This application is a continuation of application Ser. No. 829,636, filed Feb. 14, 1986 now abandoned.

In recent years topically applied medicated bandages have become increasingly important for the systemic adminstration of systemically active drugs. These patches have also been used to deliver drugs for topical administration.

Primarily, the patches can be classified in two very general groups. The first group has the drug contained in an adhesive or in a reservoir which is completely coated with an adhesive. The second group includes those patches in which the drug is within a reservoir through which the drug is soluble or a "sponge" through which it is freely transferrable and an adhesive surrounds, but does not cover, the contact area between the reservoir and the patient. Such patches are described in U.S. Pat. Nos. 3,598,122; 3,598,123; 3,731,683; 3,734,097; 3,742,951; and 3,797,494.

While these patches have proved to be quite useful, they each suffer from considerable defects. In the first group mentioned above (those with continuous adhesive layers over the reservoir or with the active substance dispersed therein), since the drug must pass through the adhesive to reach the patient's skin, only a limited number of adhesives can be advantageously employed.

If the active drug is soluble in the adhesive, the drug redistributes itself, from the reservoir into the adhesive, during storage. This results in an initial "burst" of drug exposed to the skin, yielding an initial dose much higher than would otherwise be delivered. This also means that the dose which is delivered later in time is much less than that desired. Graphically, the dose-time curve approximates the shape of that obtained with a typical single oral dose of a drug rather than the desired sustained release curve. Since one of the objects of the use of a transdermal patch is to overcome such an "initial burst", such adhesives with this type of patch have been, until the instant invention, contraindicated. Of course, if the drug in the reservoir must pass through the adhesive, an occlusive type adhesive is also ruled out. Hence, only a very limited range of adhesives have been compatible with this mode of drug administration.

In the case where the adhesive surrounds the patch drug compartment-patient contact area, problems are encountered with (1) the integrity of compartment surface-skin surface contact area (buckling of the patch away from the skin in the course of normal movement) and (2) the need for excessively large patches relative to the amount of active agent being administered. When smaller sizes are needed (due to the limited application area or for cosmetic reasons) too much of the application area is reserved for adhesive. If this "adhesive only" area is to be reduced, the adhesive used must be much stronger than would otherwise be acceptable or desirable. Such adhesives result in problems of their own. Primarily, patches employing such strong adhesives are difficult to remove, especially for those patients whose manual dexterity is compromised. In these patients, patches requiring frequent replacement are not likely to be used as regularly as recommended. Hence proper treatment is compromised.

It is an object of the invention to provide a patch for administering medication which is free of the above defects.

Another object is to provide a patch for administering medication which is compatible with a large number of alternative adhesive layers.

A further object of the invention is to provide a patch for administering medication which assures proper patch-skin contact over the patch's entire surface.

Surprisingly, it has now been found that all of these objects, and others, are realized by pattern printing a discontinuous pattern of adhesive over the external surface of an active-agent contaning compartment, which adhesive will contact the patients skin when the patch is used.

BRIEF DESCRIPTION OF THE DRAWINGS

FIG. 1 illustrates a top view a typical patch of the invention absent a protective overlayer.

FIG. 2 is a cross sectional view of FIG. 1.

FIG. 3 is an alternative embodiment of the invention absent a protective overlayer.

FIG. 4 is an alternative printing pattern on a reservoir compartment.

FIG. 5 is a cross section of FIG. 3.

DETAILED DESCRIPTION OF THE INVENTION

A typical patch 1 of the invention comprises an occlusive backing layer 2, a drug reservoir 3, an adhesive 4, and a removable protective overcoat layer 6. The backing layer does not permit the drug to travel through it and does not interact with the drug. The reservoir can be a block of material (either the drug or a formulation thereof alone or within a matrix) applied to the backing layer or contained within a membrane through which the drug can migrate. Alternatively backing layer 2 and a membrane layer 5 can define the reservoir compartment 3 therebetween. Over the external surface of reservoir 3, distal to the backing layer, is a discrete, discontinuous, adhesive layer 4. Finally, on adhesive layer 4, distal to reservoir 3 is a removalbe protective overcoat 6. The overcoat is removed by the patch user immediately prior to use thereof. Such patches, except that the adhesive layers are continuous and cover the entire reservoir-patient contact area or do not cover any of the reservoir-patient contact area, are described generally in U.S. Pat. No. 3,797,494. The shape of the patch itself, the shape of the reservoir and the number of reservoirs in a patch are not limited to the embodiments shown in the drawings. They can be of any shape and number as desired.

Essentially any pattern of adhesive (such as adhesive 4' in FIG. 4) over the surface of reservoir 3 is suitable. However, a series of adhesive dots of uniform size and spacing is most convenient. While any means of applying the adhesive pattern will suffice, pattern printing is the most preferred.

At least 20%, preferably at least 30%, more preferably about 40%, of the entire patch-patient, preferably the reservoir-patient contact area should be adhesive to assure proper adhesion. Preferably, not more than 80%, most preferably less than about 60%, most preferably about 40%, of the reservoir external surface distal to the backing layer is covered by the adhesive.

The adhesive, in addition to the discontinuous pattern actually on the reservoir, can also be placed as a discontinuous or preferably continuous border 7 around the reservoir. The continuous border of adhesive, especially if an occlusive adhesive, is an extremely advantageous embodiment in that a seal is formed to completely prevent escape of active-agent to the environment through migration around the discontinuous adhesive pattern toward the outer perimeter of the patch. In these patches, the "minimum" coverage of the adhesive set forth above can be met by the combination of the discontinuous pattern and the continuous border. Still, in these embodiments it is an important feature of the invention that no less than 10% of the reservoir surface which will form the reservoir-patient contact area have adhesive thereon. The continuous border of adhesive need be no wider than the diameter of a "typical dot" of the discontinuous pattern; however, thinner or wider bands can be used depending on particular needs or desires.

Typically useful materials for the various components of the patches of the invention are generally mentioned in U.S. Pat. No. 3,797,494.

The adhesives useful in the instant invention are virtually any medically acceptable adhesive. The only limitations thereon are that the adhesive not interact with the patch reservoir or backing material and not adversely affect the drug being administered. Such adhesives will be well known to those of ordinary skill.

The adhesives can be classified as one of three types on the basis of the drugs solubility therein: (1) occusive, (2) highly soluble, and (3) slightly or sparingly soluble. For nitroglycerin, typical occlusive adhesives include: natural or synthetic rubber based compounds such as styrenebutadiene, polyisobutylene, polybutadiene, polyisoprene, and block copolymers. Adhesives in which nitroglycerin is highly soluble include: acrylic and methacrylic resins, polyurethanes, vinyl polymers, and ethylene vinyl acetate compounds containing high levels of takifying resins (which serve as solubilizers). Of course, the sparingly solubilizing adhesives can also be utilized in the instant invention. The above classification will vary from drug to drug, but those of ordinary skill will be able to determine which class a particular adhesive falls into with regard to a particular drug without difficulty.

However, for the instant invention, such a determination is not necessary. One may employ any of those adhesive types on the basis of compatability with other patch materials and cost only.

Generally, the patches are prepared by printing a pattern of adhesive onto an adhesive releasing substrate, which substrate acts as a removable protective overcoat for the finished patch. The drug reservoir is then laid down on the adhesive layer, a backing layer applied on the reservoir, and the entire patch punched from the sheet material. If the reservoir is discrete from the backing layer, an additional suitable adhesive is applied to fix the reservoir to the backing layer or, if appropriate, the reservoir is heat sealed to the backing layer. When the reservoir is a "sack" type, a drug-permeable membrane is placed on the first applied adhesive layer and then the drug is applied. Alternatively the "sack" containing the drug can be applied to the adhesive layer as a prefabricated unit. Other alternative means of making the patches of the invention will be evident to those of ordinary skill.

As should be apparent from the above, the instant invention is suitable for use with any active ingredient which is to be delivered to the skin.

In practicing this invention one can employ any systemically active drug which will be absorbed by the body surface to which the bandage is applied, consistent with their known dosages and uses. Of course, the amount of drug necessary to obtain the desired therapeutic effect will vary depending on the particular drug used. Suitable systemic drugs include, without limitation, anti-microbial agents such as penicillin, tetracycline, oxytetracycline, chlortetracycline, chloramphenicol, and sulfonamides; sedatives and hypnotics such as pentabarbital sodium, codeine, (bromoisovaleryl) urea, carbromal, and sodium phenobarbital; psychic energizers such as 3-(2-aminopropyl)indole acetate and 3-(2-aminobutyl)indole acetate; tranquilizers such as reserpine, chlorpromazine hydrochloride, and thiopropazate hydrochloride; hormones such as adrenocorticosteroids, for example, 6 -methylprednisolone; androgenic steroids, for example, methyltestosterone, and fluoxymesterone; estrogenic steroids, for example, estrone, $17\beta$-estradiol and ethinyl estradiol; progestational steroids, for example, 17 -hydroxyprogesterone acetate, medroxyprogesterone acetate, 19-norprogesterone, and norethindrone; and thyroxine, antipyretics such as aspirin, salicylamide, and sodium salicylate; morphine and other narcotic analgesics; antidiabetics, e.g., insulin; cardiovascular Agents, e.g. nitroglycerin, and cardiac glycosides such as digitoxin, digoxin, ouabain; anti-spasmodics such as atropine, methscopolamine bromide, methscopolamine bromide with phenobarbital; antimalarials such as the 4-aminoquinolines, 9-amino-quinolines, and pyrimethamine; nutritional agents such as vitamins, essential amino acids, and essential fats; and arecoline.

Additionally, in practicing this invention one can employ a wide variety of topically active drugs consistent with their known dosages and uses. Suitable drugs include, without limitation: antiperspirants, e.g, aluminum chloride; deodorants, e.g., hexachlorophene, methylbenzethonium chloride; astringents, e.g., tannic acid; irritants, e.g., methyl salicylate, camphor, cantharides; keratolytics, e.g., benzoic acid, salicylic acid, resorcinol iodochlorhydroxyquin; antifungal agents, such as tolnaftate, griseofulvin, nystatin and amphotericin; anti-inflammatory agents, such as conticosteroids, e.g., hydrocortisone, hydrocortisone acetate, prednisolone, methylprednisolone, triamcinolone acetonide, fludrocortisone, flurandrenolone, flumethasone, dexamethasone sodium phosphate, bethamethasone valerate, fluocinolone acetonide; fluoromethalone; and pramoxine HCl; anti-neoplastic agents, e.g. methotrexate; and antibacterial agents, such as bacitracin, neomycin, erythromycin, tetracycline IICl chlortetracycline HCl, chloramphenicol, oxytetracycline, polymyxin B, nitrofuraxone, mafenide ($\alpha$-amino-p-toluenesulfonamide), hexachlorophene, benzalkonium chloride, cetalkonium chloride, methylbenzethonium chloride, and neomycin sulfate.

Of the above drugs, nitroglycerin and arecoline are especially useful.

It will be appreciated, with regard to the aforesaid list of drugs, that characterization of the drug as either "systemically or topically" active is done for purposes of convenience only. Further, a given drug can be both systemically and topically active depending upon its manner of use, variation of which will be apparent to those of ordinary skill. For example, sub therapeutic systemic levels of drugs can still be utilized for a topical effect. This is especially so when systemic dosing is rate limited by the skin and a flux enhancer is advantageously used to obtain a proper systemic dose.

In addition to the aforementioned drugs, simple pharmacologically acceptable derivatives of the drugs, such as ethers, esters, amides, acetals, salts, etc., or formulations of these drugs, having the desired polymeric permeability or transport properties can be prepared and used in practicing the invention. Drugs mentioned above can be used alone or in combination with others and each other. Of course, the derivatives should be such as to convert to the active drugs within the body through the action of body enzyme assisted transformations, pH, etc.

The instant invention will be more clearly understood from the following examples, which are of an exemplary nature only and do not limit the scope of the invention.

EXAMPLE 1

Transdermal patches having nitroglycerin as the active agent were prepared as follows:

The adhesive was pattern printed (when coverage was less than 100%) with a series of dots of uniform size and spacing. When 0% coverage is indicated, adhesive is only around the outer perimeter of the reservoir-patient contact area.

Samples differed only in terms of the adhesive used and degree of coverage of the reservoir-patent contact area. 100% coverage shows the prior art as does 0% coverage. Other % coverages are of the invention. As a control, Transderm Nitro-5 (CIBA-GEIGY), a 100% coverage product currently being marketed, is presented. The cumulative release rates of the drug in each sample are set forth in Table I below.

applied to said patient, constitutes a reservoir-patient contact area, said first adhesive being present in said region to a degree which results in at least 10% of said region to no more than about 60% of said region having said first adhesive thereon, such that at least 20% of the entire surface area which will contact said patient once said patch is applied to said patient has an adhesive thereon; said drug being insoluable in said adhesive.

2. The improvement of claim 1 wherein said reservoir-patient contact area having said first adhesive thereon has a continuous border around the perimeter of said first adhesive of a second adhesive.

3. The improvement of claim 2 wherein said second adhesive is different than said first adhesive.

4. The improvement of claim 3 wherein said second adhesive is selected from those in which said drug is readily soluble.

5. The improvement of claim 3 wherein said second adhesive is selected from those in which said drug is insoluble.

6. The improvement of claim 2 wherein said first adhesive and said second adhesive are the same.

7. The improvement of claim 1 wherein at least 20% to about 60% of said region has said first adhesive thereon.

8. The improvement of claim 1 wherein at least about 40% to about 60% of said region has said first adhesive thereon.

9. The improvement of claim 1 wherein about 40% of said region has said first adhesive thereon.

10. The improvement of claim 1 wherein said discontinuous pattern is a series of dots.

11. The improvement of claim 1 wherein said reservoir is a matrix having said drug dispersed therein.

| TRANSDERM-NITRO RELEASE RATE TESTING | | | | | | | |
|---|---|---|---|---|---|---|---|
| | Cumulative Nitroglycerin Release ($\mu g/cm^2$) | | | | | | |
| Material | 1 Hr | 4 Hr | 8 Hr | 12 Hr | 16 Hr | 20 Hr | 24 Hr |
| Control TN-5 Systems (Average of 3 production lots) | 111 | 303 | 532 | 748 | 960 | 1160 | 1348 |
| No Adhesive, 9% VA Content EVA (2 mil) | 110 | 307 | 538 | 749 | 948 | 1131 | 1306 |
| No Adhesive, 9% VA Content Oil-filled EVA (2 mil) | 120 | 305 | 524 | 725 | 906 | 1081 | 1239 |
| No Adhesive 12% VA Content EVA (2 mil) | 185 | 569 | 1005 | 1381 | 1695 | 1950 | 2153 |
| Medical Adhesive Modified S-15, | | | | | | | |
| 100% Coverage | 101 | 290 | 521 | 747 | 961 | 1156 | 1354 |
| 40% Coverage | 103 | 266 | 469 | 673 | 862 | 1052 | 1230 |
| 20% Coverage | 81 | 260 | 486 | 693 | 886 | 1059 | 1234 |
| Century CA-1028 (Acrylic), | | | | | | | |
| 100% Coverage | 398 | 609 | 800 | 971 | 1082 | 1275 | 1358 |
| 40% Coverage | 373 | 746 | 1004 | 1200 | 1378 | 1546 | 1701 |
| 20% Coverage | 181 | 439 | 690 | 906 | 1109 | 1289 | 1454 |
| Fuller HM-6677 (Kraton) | | | | | | | |
| 100% Coverage | 35 | 63 | 83 | 110 | 131 | 149 | 167 |
| 40% Coverage | 85 | 241 | 436 | 620 | 793 | 963 | 1118 |
| 20% Coverage | 66 | 224 | 420 | 604 | 783 | 948 | 1106 |
| Century GI-1 (Kraton) | | | | | | | |
| 100% Coverage | 3 | 9 | 7 | 23 | 29 | 34 | 34 |
| 40% Coverage | 65 | 196 | 350 | 498 | 637 | 772 | 902 |
| 20% Coverage | 90 | 271 | 500 | 712 | 918 | 1113 | 1301 |

What is claimed is:

1. In a dermal or transdermal drug delivery system comprising a drug occlusive backing layer, a drug reservoir thereon and a first adhesive to affix (1) said drug reservoir and occlusive backing layer to (2) a patient such that drug contained in said reservoir can be delivered by said system to said patient, and a removable drug occlusive layer on said adhesive, the improvement comprising said first adhesive being in a discrete, discontinuous pattern in a region which, when said patch is 12. The improvement of claim 1 wherein said reservoir is a volume defined by said backing layer and a drug permeable porous membrane fused thereto along the periphery thereof, said drug being contained within said volume so defined.

13. The improved of claim 1 wherein said reservoir is a volume defined by a drug-permeable porous membrane and a secondary membrane, said reservoir being oriented such that when said patch is applied to said patient, said porous membrane is closer to said patient than said secondary membrane, said drug being within said volume so defined.

14. The improvement of claim 1 wherein said discontinuous pattern is a series of crosses.

15. In a dermal or transdermal drug delivery system comprising a drug occlusive backing layer, a drug reservoir thereon and a first adhesive to affix (1) said drug reservoir and occlusive backing layer to (2) a patient such that drug contained in said reservoir can be delivered by said system to said patient, and a removable drug occlusive layer on said adhesive, the improvement comprising said first adhesive being in a discrete, discontinuous pattern in a region which, when said patch is applied to said patient, constitutes a reservoir-patient contact area, said first adhesive being present in said region to a degree which results in at least 10% of said region to no more than about 60% of said region having said first adhesive thereon, such that at least 20% of the entire surface area which will contact said patient once said patch is applied to said patient has an adhesive thereon; said drug being soluable in said adhesive.

16. The improvement of claim 15 wherein said reservoir-patient contact area having said first adhesive thereon has a continuous border around the perimeter of said first adhesive of a second adhesive.

17. The improvement of claim 16 wherein said first adhesive and said second adhesive are the same.

18. The improvement of claim 15 wherein at least 20% to about 60% of said region has said first adhesive thereon.

19. The improvement of claim 15 wherein at least about 40% to about 60% of said region has said first adhesive thereon.

20. The improvement of claim 15 wherein about 40% of said region has said first adhesive thereon.

21. The improvement of claim 16 wherein said second adhesive is selected from those in which said drug is insoluble.

22. The improvement of claim 15 wherein said discontinuous pattern is a series of dots.

23. The improvement of claim 15 wherein said reservoir is a matrix having said drug dispersed therein.

24. The improvement of claim 15 wherein said reservoir is a volume defined by said backing layer and a drug permeable porous membrane fused thereto along the periphery thereof, said drug being contained within said volume so defined.

25. The improved of claim 15 wherein said reservoir is a volume defined by a drug-permeable porous membrane and a secondary membrane, said reservoir being oriented such that when said patch is applied to said patient, said porous membrane is closer to said patient than said secondary membrane, said drug being within said volume so defined.

26. The improvement of claim 15 wherein said second adhesive is different than said first adhesive.

27. The improvement of claim 15 wherein said second adhesive is selected from those in which said drug is readily soluble.

28. the improvement of claim 15 wherein said discontinuous pattern is a series of crosses.

* * * * *